US006221386B1

(12) United States Patent
Cherwonogrodzky et al.

(10) Patent No.: US 6,221,386 B1
(45) Date of Patent: Apr. 24, 2001

(54) USE OF VIRULENCE FACTORS OF PATHOGENS TO IMPROVE LIPOSOMAL DELIVERY OF THERAPEUTIC AGENTS

(75) Inventors: John Cherwonogrodzky; Jonathan P. Wong, both of Medicine Hat; Vincent L. Dininno, Radcliff, all of (CA)

(73) Assignee: Her Majesty the Queen in right of Canada, as represented by the Minister of National Defence, Ottawa (CA)

( * ) Notice: Subject to any disclaimer, the term of this patent is extended or adjusted under 35 U.S.C. 154(b) by 0 days.

(21) Appl. No.: 09/251,304

(22) Filed: Feb. 17, 1999

Related U.S. Application Data

(63) Continuation-in-part of application No. 08/782,129, filed on Jan. 13, 1997, now abandoned.

(30) Foreign Application Priority Data

Mar. 8, 1996 (CA) ..................................................... 2171369

(51) Int. Cl.[7] ..................................................... A61K 9/127

(52) U.S. Cl. .................. 424/450; 424/234.1; 424/236.1; 424/241.1; 424/252.1; 424/257.1; 424/258.1; 424/260.1; 424/812; 436/829; 514/54; 514/885

(58) Field of Search ................................ 424/450, 234.1, 424/236.1, 241.1, 252.1, 257.1, 258.1, 260.1, 812; 436/829; 514/54, 885

(56) References Cited

U.S. PATENT DOCUMENTS

| | | |
|---|---|---|
| 4,394,448 | 7/1983 | Szoka . |
| 4,873,088 | 10/1989 | Mayhew . |
| 5,215,917 | 6/1993 | De Araujo . |

FOREIGN PATENT DOCUMENTS

| | | |
|---|---|---|
| 2109952 | 12/1992 | (CA) . |
| 2101241 | 1/1995 | (CA) . |

OTHER PUBLICATIONS

Veterinary Immunology and Immunopathology (1985); Dees, C. et al; pp. 171–182 "Enhanced Intraphagocytic Killing of *Brucella Abortus* in Bovine Mononuclear Cells et al"..

Infection and Immunity, Jul. 1990; Detilleux et al; pp. 2320–2328; "Penetration and Intracellular Growth of *Brucella abortus* in Nonphagocytic Cells in Vitro".

Am J Vet Res, vol. 50 No. 9, Sep. 1989; Hernandez–Casseles et al; pp. 1486–1488, "Treatment of *Brucella melitensis* infection in mice by use of lipsome–encapsulated gentamicin".

Journal of Immunological Methods; 1988; Dijkstra et al; pp. 197–205, "A procedure for the efficient incorporation of wild–type lipopolysaccharidde into liposomes for use in et al".

Infection and Immunicty, Jan. 1989; Kuhn et al; pp. 57, 55–61; "Identification of an Extracellular Protein of *Listeria monocytogenes* Possibly involved in intracellular Uptake by Mammalian Cells".

Animal Brucellosis (1990); Cherwonogrodzky et al; pp. 19–64; :Antigens of Brucella.

Aids Research and Human Retroviruses, vol. 7, No. 5, 1991; Golding et al; pp. 435–446; Production of a Novel Antigen by Conjuction of HIV–1 to *Brucella abortus*: Studies of Immunogenicity, et al.

Infection and Immunity, vol. 60. No. 4Apr. 1992; Goldstein et al; pp. 1385–1389; "Lipopolysaccharide (LPS) from *Brucella abortus* is Less Toxic than That from *Escherichia coli* et al".

Cancer Research 42, Jan. 1982, Schroil et al; pp. 161–167; "Effects of Liposome Structure and Lipid Composition On The Activation of the Tumoricidal Properties of Macrophages by Liposomes et al".

Liposomes; 1983; Ostra, Marc J.; pp. 289–341; Liposomes.

The Journal of Infectious Diseases, vol. 132, No. 3, Sep. 1985; Fountain et al; pp. 529–535; "Treatment of *Brucella canis* and *Brucella aborus* in Vitro and in Vivo by Stable Plurilamellar et al".

Animal Brucellosis Brucellosis: Clinical and Laboratory Aspects; 1989; Young, Edward J.; pp. 127–141; "Treatment of Brucellosis in Humans".

Animal Brucellosis, 1990; Sutherland et al; pp. 65–81 "The Immune Response to *Brucella Abortus*: The Humoral Response".

*Primary Examiner*—Gollamudi S. Kishore
(74) *Attorney, Agent, or Firm*—Nixon & Vanderhye P.C.

(57) ABSTRACT

Liposome encapsulated antibiotic therapy has limited application against infectious organisms, which can sequester in non-phagocytic cells. Virulence factors of these infectious organisms, for example bacterial components, when used in the formulation of liposomes can enhance the effectiveness of liposomes as delivery systems in the treatment of disease. In this manner, multi-functional liposomes can be developed to treat target diseases. In addition to serving as antibiotic delivery systems, such liposomes also have an immunization effect. Thus, the liposomes can be used for both the prevention and treatment of diseases.

12 Claims, No Drawings

USE OF VIRULENCE FACTORS OF PATHOGENS TO IMPROVE LIPOSOMAL DELIVERY OF THERAPEUTIC AGENTS

This application is a continuation-in-part of application Ser. No. 08/782,129 filed Jan. 13, 1997 now abandoned.

FIELD OF THE INVENTION

The present invention relates to a liposomal delivery of a therapeutic agent and is particularly concerned with the use of virulence factors of pathogens to improve the liposomal delivery of the therapeutic agent.

BACKGROUND OF THE INVENTION

Brucellosis is a zoonotic disease that afflicts, depending on the region, about 5% of the livestock around the world. Although cattle, swine, sheep, goats and dogs are the usual hosts (with *B. abortus, B. swis, B. ovis, B. melitensis* and *B. canis* being the usual agents, respectively), the impact of brucellosis may be far greater as it can also infect other animals such as poultry and marine mammals, The manifestation of these bacteria in animals are usually reproductive complications (aborted fetuses, inflammed uterus or orchitis, sterility). Brucella is a bacterium that can become a facultative parasite, invading cells of the blood, bone marrow, organs and skeletal tissue. It is difficult to eliminate and relapses of infections may occur once antibiotic treatment ceases. Vaccination in animals has proven partially effective in offering protection, though these vaccines are pathogenic for other animals and humans.

Because it is a highly infective organism that causes debilitating symptoms, Brucella can persist in the environment for months under the right conditions, and as there are no effective vaccines or therapeutic recourses, it is potentially a bacterial warfare agent. There is, therefore, an urgent need to develop a means for protecting or treating people at risk.

Although antibiotics are effective in inhibiting or killing pathogens, they are less effective against pathogens that infect and then become intracellular parasites within animal or human hosts. Rather than being destroyed by white blood cells, the Brucella species, for example, thrive within these cells. Antibiotics are available that will inactivate Brucella species, but these are effective only in the test tube. In vivo, the bacterium will invade cells of the reticulo-endothelial system and become a facultative parasite, rendering it protected and difficult to eat. Antibiotics are limited in their effectiveness due to the following reasons:

- only a small portion of the antibiotic may reach the infected cell due to its dilution throughout the body;
- some antibiotics may not be able to cross the mammalian cell membrane barrier;
- the antibiotic may be excreted through the urine; and,
- some antibiotics may become inactivated by serum or cellular enzymes.

Current research in liposome encapsulation of antibiotics has brought in a new era in the therapy of disease. Liposomes are microscopic pockets of lipids that can be used to entrap antibiotics and to deliver these into phagocytic cells. The advantages of such a process are:

- liposomes contain the antibiotic and prevent its dilution within the body or secretion in the urine;
- these lipid vesicles are also phagocytized and will be delivered to the site where the pathogen has sequestered; and,

- the liposomes are made of bio-degradable lipids and are non-toxic. Indeed, these may shield the body from the harmful side-effects of toxic antibiotics, The use of liposomes as an antibiotic delivery system is described in the inventors co-pending Canadian application no. 2,101,241 (published Jan. 24, 1995) wherein liposome encapsulated ciprofloxacin was found to be more effective in the prevention and treatment of *Francisella tularensis* infection than the nonencapsulated antibiotic.

Further, the use of multiple doses of negatively charged liposomes as carriers of gentamicin into cells have been reported but these were only partially effective in vivo (Dees, C. et al., 1985, *Vet. Immunol. Immunopathol.,* 8, 171–182), possibly because liposomes require phagocytosis for delivery and Brucella can invade even non-phagocytic cells (Detilleux, P. G. et al., 1990, *Infect. Immun.,* 58, 2320–2328). Non-phagocytic cells are unlikely to engulf liposomal antibiotics and so will protect their intra-cellular parasites from these therapeutic agents. Other antibiotics will liposomes have proven effective against some strains of Brucella (e.g. *B. canis* and *B. abortus*) but less so against another strain (e.g. *B. melitensis*) (Hernandez-Caselles, T. et al., 1989, *Am. J. Vet. Res.,* 50. 1486–1488). The treatment of the latter strain with antibiotics requires liposomes of a positive rather than negative charge, requires multiple treatments to be effective and although the organism may appear eliminated in mice 5 days after treatment, relapses are a possibility.

Gregoriadis, in Canadian application no. 2,109,952 (published Dec. 23, 1992), describes the use of polysaccharide coated liposomes as drug delivery agents. It is described that such polysaccharide coating is used to increase the residence time of liposomes in vivo thereby prolonging the availability of the drug. However, this reference does not address the issue of such liposomes entering non-phagocytic cells. The use of lipopolysaccharide (LPS) with liposomes has been described by Djikstra et al. (1988, *J. Immunol. Meth.,* 114, 197–205) but the LPS was typically water-soluble and housed within the liposome rather than part of the liposome's composition.

Thus, antibiotic therapy of some diseases is very limited due to the protection offered when the facultative parasites are intracellular. Liposome encapsulation of these antibiotics enhances their effectiveness, but the indication is that there is a need for "designer" liposomes, or specific formulations of liposomes for different diseases.

SUMMARY OF THE INVENTION

It is an object of the present invention to provide a new microsphere formulation, which includes the virulence factors such as O-polysaccharide or lipopolysaccharide of bacteria. Preferably, the microsphere is a liposome consisting of phosphatidylcholine, cholesterol, and phosphatidylserine in a molar ratio of 7:2:1. Suitable bacteria are selected from the group consisting of *Vibrio cholorae, Yersinia entierocolitica* O:9, toxigenic *Escherichia coli* O:157H:7, *Salmonella landau, Pseudomonas maltophilia* 555 and Brucella such as *B. abortus* or *B. melitensis.* The microsphere formulation according to the present invention has enhanced effectiveness as delivery systems for antibiotics in the treatment of disease.

Thus, the invention provides for the use of virulence factor in the formulation (in combination with or in the replacement of lipids) of microspheres and specifically in liposomes.

Further, the invention provide for a pharmaceutical formulation for preventing or treating infections wherein a therapeutic agents are encapsulated by liposomes comprised in part by virulence factors such as bacterial components.

The invention also provides a method of increasing the uptake of a composition in an mammal comprising administering to the mammal the composition, wherein the composition comprises a therapeutic agent entrapped within a microsphere, for example, a liposome comprising a bacterial component selected from the group consisting of O-polysaccharide and lipopolysaccharide. Preferably, the bacterial component is incorporated into or onto the membrane of the microsphere.

In one embodiment of the invention, the composition is taken-up by non-phagacytic cells.

In accordance with another aspect of the invention, there is provided a method of treating a mammal against brucellosis comprising administering to said mammal a liposomal formulation comprising a bacterial component selected from the group consisting of O-polysaccharide and lipopolysaccharide incorporated into or onto the membrane of said liposome to enhance the uptake of said liposomal formulation by non-phagocytic cells of said mammal.

DETAILED DESCRIPTION OF THE PREFERRED EMBODIMENT

Since some bacteria have mechanisms for invading host cells (Kuhn, M. and W. Goebel, 1989, *Infect. Immun.,* 57, 55–61) it was speculated that these virulence factors could be used to improve liposomes for the delivery of antibiotics into mammalian cells. As several pathogenic bacteria have the same rare sugar on their cell surfaces as Brucella (Cherwonogrodzky, J. W. et al., 1990, in *Animal Brucellosis,* K. Nielson and J. R. Duncan (ed.), 19–64), it is likely that their smooth-lipopolysaccharides (S-LPS) have something to do with their invasiveness into cells. Virulence factors include enzymes (e.g. proteases of the flesh-eating bacterium), toxins (e.g. diphtheria toxin), binding components (e.g. Protein A of *Staphlococcus aureus*) and invasive factors (e.g. the protein "invasin" from *Listeria monocytogenous,* the lipopolysaccharide of Brucella and the glycoproteins of some viruses).

Further, the invention will be described with specific reference to liposomes. However, the invention is applicable to any microsphere. By microsphere it is meant any microscopic vesicle capable to carrying antibiotics, drugs etc. Some examples are nylon beads, polymers of amino acids or carbohydrates, globules of detergents and "bubbles" of lipids or liposomes.

Thus, it will be shown that virulence factors (such as bacterial components) can be included in the composition of liposomes to improve their effectiveness as delivery systems of therapeutic agents against specific diseases. Proof of this concept is given in the following study that uses the bacterial component lipopolysaccharide with exceptional properties (hydrophobic rather than hydrophilic, associated with invasive properties, low toxicity).

EXAMPLE 1

Protection and Treatment Studies of BALB/c Mice 1.1 Bacterium

*Brucella melitenis* 16M was acquired from Agriculture Canada, Animal Diseases Research Institute, Nepean, Ontario. It was maintained on Brucella agar with 1.4 ppm crystal violet, 37° C., 5% $CO_2$. The strain used was passed once through a mouse and isolated from its spleen. Prior to use, a single colony of bacteria was sub-cultured on trypticase soy agar without crystal violet, incubated for three days, and then this fresh growth, suspended in sterile 1% saline, was used to infect mice. Previous studies showed that a suspension having an O.D.620 of 0.1 had $1\times10^9$ colony forming units (CFU)/ml. Dilutions of $2.5\times10^5$ CFU/ml were made and 0.2 ml of this was used to infect each mouse.

1.2 S-LPS

*Brucella melitensis* 16M S-LPS was purified by the method of Cherwonogrodzky et al. (1990). Briefly, a culture was grown in Brucella broth, killed with 2% phenol, then following centrifugation, the supernatant was saved and crude S-LPS was precipitated with S volumes of methanol with 1% sodium acetate (w/v). The precipitate was collected by centrifugation, dialysed against TRIS buffer (pH 7), then digested with lysozyme, RNAse, DNAse and proteinase K. A phenol-water extraction was done, the phenol layer was removed, and the S-LPS was precipitated and washed with methanol-acetate. The preparation was dialysed, ultracentrifuged overnight at 120,000×g and the pellet was re-suspended in distilled water, then lyophilized.

1.3 Preparation of Liposomes with S-LPS

The basic liposome was prepared by dissolving in 2:1 chloroform and methanol, the lipids phosphatidylcholine:cholesterol:phosphatidylserine (AvantiLipidsInc., Birmingham, Ala.) in a molar ratio of 7:2:1 (a total of 20 μmoles were used, respective molecular weights are 810:387:745, amounts used were 11.34 mg:1.55 mg:1.49 mg all in 1 ml). The lipid solution was dried to a thin film on the bottom of a large screw-capped tube by heating at 45° C. in a heating block. Throughout this procedure, the content of the tube was purged with a gentle stream of dry nitrogen. The lipids were then further dried for 30 min. in a vacuum chamber to remove any remaining organic solvent. The S-LPS (10 mg in 1 ml phosphate buffered saline, pH 7) was sonicated in a bath type sonicator for approximately 3 min. or until the S-LPS solution became homogenous. Part of the dispersed S-LPS solution was added to the tube containing the dried lipid mixture. Ciprofloxacin (Miles Canada Inc., Etobicoke, Ontario) or tetracycline (Sigma Chemical Co., St. Louis, Mo.) was made at 20 mg/ml distilled water and of this 2 ml was added to the tube. The contents of tie tube were mixed vigorously by vortexing and heating at 45° C. The vortexing-heating cycle was repeated about 15–25 times, under dry nitrogen, until the dried lipids were completely dislodged from the sides of the tube (about 20 min. is required for this procedure). The lipid-antibiotic-LPS mixture was gently sonicated as before for approximately 2 min. and was then rapidly frozen in a dry ice-methanol mixture. The sample was then freeze-dried overnight in a lyophilizer (Virtis Company Inc., Gardiner, N.Y.). The freeze-dried mixture was reconstituted in 0.5 ml of distilled water. The reconstituted liposomes were then vortexed for 2 to 3 minutes under nitrogen and were left undisturbed at room temperature for 1 hour. The liposomes were washed with 8 ml of distilled water then ultra-centrifuged at 125,000×g for 30 min at 4° C. The pellet was re-suspended in distilled water, ultra-centrifuged as before, and then reconstituted in distilled water. Encapsulation was about 50% efficient and so 4 ml of water gave a suspension of 5 mg/ml (1 mg/0.2 ml was used to treat each mouse). The preparation was used immediately.

1.4 Animal Studies 5 week old BALB/c mice (15–16 g) were obtained from Charles River Canada Inc. (St. Constant, Quebec) and were left in quarantine at least a week before use. Intravenous injections were done at the tail vein, intramuscular injections were at a thigh muscle Throughout the study, the mice were housed in Horsfal™ units and cared for under the Canadian Council on Animal Care guideline. At the end of the study, the animals were sacrificed by cervical dislocation, their spleens were aseptically removed, crushed in 2 ml sterile saline with a manual tissue grinder (Wheaton, Millville, N.J.), then diluted in saline and plated onto Brucella agar with crystal violet. The plates were incubated as before and inspected 3 and 7 days later.

1.5 Results and Discussion

Upon testing negatively-charged liposomes in the delivery of ciprofloxacin (LIP-Cipro, or liposome encapsulated ciprofloxacin) for the prophylaxis and treatment of mice given $LD_{50}$ of *Francisella tularensis* LVS, the animals were rescued from certain death, even when only a single dose of LIP-Cipro was given (as described in Canadian patent number 2,101,241).

Upon testing the same formulation against *B. melitensis* 16M, it appeared to be neither protective nor therapeutic against this disease as illustrated in Tables 1 and 2 respectively. This supports the study by Dees et al. (1985) who showed that even multiple doses of antibiotic within liposomes cannot eliminate brucellosis in vivo. This limitation is understandable in that Brucella has been found to have the ability to invade even non-phagocytic cells Hernandez-Caselles et al., 1989). It therefore can invade, sequester and grow within tissues that liposomes of the usual formulation cannot reach.

The mechanism by which Brucella species can penetrate the noted cells is unknown. However, it has been observed that several invasive pathogens (e.g. *Vibrio cholerae, Yersinia enterocolitica* 0:9, enterotoxigenic *Escherchia coli* 0:157H:7, *Salmonella landau, Pseudomonas maltophilia* 555) have derivatives of a rare sugar (4-amino-4,6-alpha-D-mannopyrannose (Cherwonogrodzky et al., 1990), also found on Brucella on their O-polysaccharide which forms part of the smooth-lipopolysaccharide (S-LPS) that coats these bacteria. On the chance that liposomes, with this antigen as part of their composition, would gain an advantage in being delivered to similar sites as viable Brucella, we formulated a novel liposome that had *B. melitensis* S-LPS as part of its composition. It should be noted that this S-LPS differs from the S-LPS of several other bacteria in that it is hydrophobic and is readily incorporated with the other lipids in liposome formulation. Table 3, for the protection against diseases, and Table 4, for the treatment of infected mice, show tat multiple doses of liposomes having S-LPS in their composition and used to encapsulated antibiotics, such as ciprofloxacin or tetracycline, were effective in greatly reducing the number of bacteria. Table 3 shows that this result is temporary, possibly due to other sites in the animal providing a source of infection. There is also some protection given by S-LPS given with tetracycline, in the absence of liposomal formulation. This latter observation may be due to the ability of S-LPS to spontaneously form structures that may entrap or associate with tetracycline. The evidence suggests that virulence factors, in this case Brucella S-LPS, may replace part or all of the lipids used in liposome formulation.

Although the embodiment described herein relates to the use of S-LPS in the formulation of liposomes, the same results may also be obtained by using other virulence factors (i.e. bacterial components such as rough-lipopolysaccharide, outer-polysaccharide, lipids, or proteins) or bacterial components linked to carriers (i.e. O-polysaccharide linked to proteins such as bovine serum albumin) or modified bacterial components (i.e. alkaline treated S-LPS, detoxified LPS, cloned protein fragments). Further, the virulence factors can be used with, or replace part or all of the lipids used in the formulation of liposomes.

It is believed that the present invention may have several applications:

1) For diseases (bacteria, rickettsiae, viruses, fungi, parasites) which are difficult to treat, "designer" liposomes may be formulated by extracting components from these pathogens and incorporating these in the formulation of delivery systems. The components could be used intact, fragmented, or coupled to carriers before being used. The components do not have to be characterized, and if cross-reactive, may be used in the treatment or protection against more than one pathogen. This, by incorporating whole, modified, or fragments of cellular components of the pathogen into the liposome formulation, one may improve the effectiveness of this delivery system.

2) Potentially, a liposome or microsphere formulated with this technology could be multi-functional (i.e. the invasive factor in the liposomal composition may assist delivery within cells as well as serve as a vaccine, this novel liposomal formulation may be used to entrap antibiotics, immunomodulators or drugs). In the embodiment described herein, the S-LPS component is used to enhance either the stability or delivery of the liposome to sites of infection. The S-LPS is also a strong antigen. One could therefore have a liposome or microsphere that serves as a more effective delivery system, provides antigen as a vaccine, encapsulates antibiotics for treatment and may have some immunomodulation effect. For example, this type of multi-functional liposome or microsphere has an invasive factor and/or a vaccinating agent incorporated within its structure and is used to deliver antibiotics, drugs, antibodies and/or immunomodulators. The use of this new formulation may greatly enhance prophylaxis against disease or its treatment.

3) Further, such multi-functional liposomes may have significant impact on difficult diseases. In the example of AIDS research, inactivated HIV coupled to *B. abortus* gives 6 fold better immunization that inactivated HIV alone (Golding, B. et al., 1991, *AIDS Res. Hum. Retrovir.,* 7, 435–446). Potentially, a liposome, with *B. abortus* or *B. melitensis* LPS as part of its formulation, that encapsulates inactivated HIV, anti-viral agents, antibodies from HIV-positive/AIDS-negative patients, immunomodulators or a combination thereof may be even more effective. Also, one may have the HIV antigen as part of the liposome formulation that encapsulates anti-viral antibiotics such as AZT. It should be noted that the Brucella LPS is about 1000-fold less toxic than other bacterial S-LPS (Goldstein et al., 1992, *Infect. Immun.,* 60, 1385–1389) and would be ideal for this formulation.

TABLE 1

Protection studies of BALB/c mice given single doses of antibiotics at different times before infection with *Brucella melitensis* 16M[1]

| Antibiotic | Time Before Infection (days) | *B. melitensis* 16M counts in spleens 7 days after infection |
|---|---|---|
| Control | — | $1.0 \pm 0.3 \times 10^4$ |
| Ciprofloxacin | 7 | $1.9 \pm 0.4 \times 10^4$ |
| | 3 | $1.4 \pm 0.2 \times 10^4$ |
| | 2 | $2.8 \pm 1.0 \times 10^4$ |
| | 1 | $1.5 \pm 0.3 \times 10^4$ |
| Liposome-encapsulated | 7 | $3.4 \pm 1.0 \times 10^4$ |
| Ciprofloxacin (LIP-Cipro) | 3 | $2.3 \pm 0.5 \times 10^4$ |
| | 2 | $3.9 \pm 1.4 \times 10^4$ |
| | 1 | $2.9 \pm 1.1 \times 10^4$ |

[1]A total of 1 mg ciprofloxacin in 0.2 ml saline/mouse (3 mice/set) was given intramuscularly at the times noted. The mice were then infected with $5 \times 10^4$ colony forming units (CFU) of *B. melitensis* 16M.

TABLE 2

Treament studies of BALB/c mice given single doses of antibiotics at different times after infection with *Brucella melitensis* 16M[1]

| Antibiotic | Time Before Infection (days) | *B. melitensis 16M counts in* spleens 7 days after infection |
|---|---|---|
| Control | — | $1.0 \pm 0.3 \times 10^4$ |
| Ciprofloxacin | 1 | $1.6 \pm 0.3 \times 10^4$ |
| | 2 | $13.0 \pm 0.6 \times 10^4$ |
| | 3 | $3.5 \pm 0.9 \times 10^4$ |
| | 7 | $3.9 \pm 1.6 \times 10^4$ |
| Liposome-encapsulated | 1 | $2.8 \pm 0.9 \times 10^4$ |
| Ciprofloxacin (LIP-Cipro) | 2 | $2.0 \pm 0.7 \times 10^4$ |
| | 3 | $2.4 \pm 0.8 \times 10^4$ |
| | 7 | $26 \pm 0.7 \times 10^4$ |

[1]Same procedure as in Table 1.

TABLE 3

Protection studies of BALB/c mice given multiple doses of antibiotics at different times before infection with *Brucella melitensis* 16M[1]

| Antibiotic2 | Time Before Infection (days) | *B. melitensis* 16M counts in spleens: 3 Days after Infection | 11 Days after Infection |
|---|---|---|---|
| Control: no treatment | — | $3.6 \pm 0.9 \times 10^4$ | $1.0 \pm 0.4 \times 10^4$ |
| Control: | 7,3,2,1 | $1.2 \pm 0.4 \times 10^3$ | $2.1 \pm 0.7 \times 10^4$ |
| LIP-LSP | 3,2,1 | $2.3 \pm 0.7 \times 10^4$ | $4.3 \pm 0.3 \times 10^4$ |
| | 2,1 | $8.0 \pm 2.0 \times 10^3$ | $1.1 \pm 0.8 \times 10^5$ |
| | 1 | $5.4 \pm 0.8 \times 10^4$ | $1.6 \pm 0.6 \times 10^5$ |
| Control: | 7,3,2,1 | $4.3 \pm 0.3 \times 10^2$ | $3.6 \pm 1.8 \times 10^3$ |
| TETRA-LPS | 3,2,1 | $7.0 \pm 3.8 \times 10^3$ | $1.2 \pm 1.0 \times 10^4$ |
| | 2,1 | $1.8 \pm 3.8 \times 10^4$ | $1.7 \pm 0.5 \times 10^4$ |
| | 1 | $7.9 \pm 2.5 \times 10^4$ | $3.5 \pm 0.3 \times 10^4$ |
| | 7,3,2,1 | 0 | $1.2 \pm 1.2 \times 10^3$ |
| LIP-CIPRO-LPS | 3,2,1 | 0 | $1.0 \pm 0.8 \times 10^3$ |
| | 2,1 | $1.0 \pm 1.0 \times 10^1$ | $3.3 \pm 0.9 \times 10^3$ |
| | 1 | $1.8 \pm 0.8 \times 10^3$ | $1.0 \pm 0.4 \times 10^3$ |
| | 7,3,2,1 | $7.5 \pm 0.9 \times 10^2$ | $1.8 \pm 1.8 \times 10^3$ |

TABLE 3-continued

Protection studies of BALB/c mice given multiple doses of antibiotics at different times before infection with *Brucella melitensis* 16M[1]

| Antibiotic2 | Time Before Infection (days) | *B. melitensis* 16M counts in spleens: 3 Days after Infection | 11 Days after Infection |
|---|---|---|---|
| LIP-TETRA-LPS | 3,2,1 | $1.9 \pm 0.2 \times 10^3$ | $9.0 \pm 1.2 \times 10^3$ |
| | 2,1 | $3.1 \pm 1.1 \times 10^3$ | $1.9 \pm 0.1 \times 10^4$ |
| | 1 | $3.0 \pm 0.6 \times 10^3$ | $2.8 \pm 1.6 \times 10^4$ |

[1]Same as for Table 1, except 2 mice were used per set. Protection is defined as causing a log10 less CFU as controls.
[2]Antibiotic abbreviations are:
a) LIP-LPS for liposomes made with *B. melitensis* smooth-lipopolysaccharide (S-LPS) and no antibiotic;
b) TETRA-LPS is non-encapsulated tetracycline and S-LPS;
c) LIP-CIPRO-LPS is ciprofloxacin encapsulated in liposomes made with S-LPS, and
d) LIP-TETRA-LPS is tetracycline encapsulated in liposomes with S-LPS.

TABLE 4

Treatment studies of BALB/c mice given multiple doses of antibiotic at different times after infection with *Brucella melitensis* 16M[1]

| Antibiotic | Spleen counts after antibiotic was given by the following routes: Intramuscular | Intravenous |
|---|---|---|
| Control: no treatment | $2.4 \pm 0.3 \times 10^4$ | $2.4 \pm 0.3 \times 10^4$ |
| Control: LIP-LPS | $2.1 \pm 0.5 \times 10^4$ | $2.1 \pm 0.5 \times 10^4$ |
| Tetracycline[2] | $4.8 \pm 0.8 \times 10^3$ | $4.1 \pm 0.6 \times 10^3$ |
| TETRA-LIP | $3.2 \pm 1.4 \times 10^3$ | $4.4 \pm 0.3 \times 10^3$ |
| TETRA-LIP-LPS | — | $4.7 \pm 0.9 \times 10^2$ |
| Ciprofloxacin | $1.3 \pm 0.4 \times 10^4$ | $2.0 \pm 0.6 \times 10^4$ |
| CIPRO-LIP | $1.1 \pm 0.1 \times 10^4$ | $1.4 \pm 0.2 \times 10^4$ |
| CIPRO-LIP-LPS | — | $8.1 \pm 4.9 \times 10^3$ |

[1]For each set, three mice were infected with 5 × 104 colony forming units (CFU) of *Brucella melitensis* intravenously on day 0. Treatments consisted of a dose of I mg antibiotic/0.2 ml and were given on days 7, 8 and 9. The mice were sacrificed on day 12, the spleens were harvested, crushed in saline and then plated.
[2]All antibiotics were given at 1 mg/mouse. TETRA = tetracycline, CIPRO = ciprofloxacin, LIP = liposome encapsulated, LPS = *B. melitensis* 16M smooth-lipopolysaccharide in liposome formulation.

EXAMPLE 2

Uptake of Liposomal Formulation within Tissue Culture 2.1 Preparation of Liposome Formulations

*Brucella abortus* strain 1119-3 O-polysaccharide (OPS) and *Brucella melitensis* strain 16M smooth-lipopolysaccharide (LPS) were prepared by conventional methods (Cherwonogrodzky, J. W., G. Dubray, E. Moreno and H. Mayer. 1990. Antigens of Brucella (Chapter 2). In K. Nielsen and J. R. Duncan, Animal Brucellosis, CRC Press, Boca Raton, USA, pages 52–55). *Brucella melitensis* strain 16M smooth-lipopolysaccharide completed with protein (LPS-protein) was prepared in a manner similar to LPS except that while LPS does not precipitate in the presence of 0.2M trichloroacetic acid, LPS-protein does. The latter was then dialyzed against distilled water and freeze-dried.

L-α-phosphatidylcholine (PC) was purchased from Avanti Polar Lipids (Alabaster, Ala.). Cholesterol (CH) was purchased from Sigma Chemical Co. (St. Louis, Mo.) and radioactive ciprofloxacin was acquired from Bayer-Miles Canada Inc. (Etobicoke, ON).

For each batch of liposome (6 ml total volume), 251 mg of PC and 104 mg of CH was added to a round bottom flask and 4 ml of chloroform was added to dissolve the lipids. This was rotor-evaporated in a 45° C. water bath to form a thin film. This was dried in a vacuum incubator at 60° C., less than 80 Kpa, for 2 hours. A given Brucella compound (7 mg) was suspended in 4.5 ml of 600 mM ammonium sulfate solution, sonicated (5 cycles of 30 seconds and 5 $\mu$m amplitude with a 60 seconds pause between cycle) filtered through a 0.22 $\mu$m filter and this suspension was also used to rehydrate the lipids. The suspension was frozen in liquid nitrogen, thawed in a 45° C. water bath, and freeze-thawed a total of 5 times. This improves the liposomal formulations by reducing their size and making stable forms. The freeze-thawed suspension was extruded 10 times through a 0.22 $\mu$m filter under 4000 Kpa pressure and then the suspension was dialyzed for 15 hrs at 23° C. against 0.9% saline. The dialyzed liposomes were then removed and to this was added 30 mg of radioactive ciprofloxacin (15 $\mu$Ci) and 103 mg of non-radioactive ciprofloxacin in 0.6 ml of saline. The preparation (about 6.5 ml) was heated in a 45° C. water bath for 1 hour with gentle mixing then let stand at 23° C. for 2 hours. The warm temperature allows entrapment of the ciprofloxacin into the liposome. The liposomes were washed with saline. The suspension was centrifuged at 50,000 rpm, the supernatant was removed and the liposomal pellet was resuspended in saline. This was centrifuged again and the liposomal were then resuspended. By comparing the radioactivity within the liposomes and the total radioactivity (liposome and removed supernatant) the entrapment efficiency of the radioactive antibiotic was found to be 81%. The liposomal suspension was stored in a small bottle that was purged with nitrogen gas, then scaled and kept at 4° C., ready to be used 2.2 Tissue Culture Assay Vero cells (prepared from African green monkey kidneys) were subculture in DMEM media with 10% fetal calf serum and antibiotic supplements (DMEM-FCA). When required, cells were detached from the flask with trypsin, pelleted by using a bench top centrifuge (5000 rpm for 5 min at 23° C.), the supernatant was discarded and the cells were resuspended in fresh DMEM-PCA then counted under the microscope. 14 tissue culture plates (12 for the liposomal tests, 2 for controls) were seeded with 700,000 cells/well and incubated overnight at 37° C. with 5% $CO_2$.

At the time of the experiment, a microscopic examination showed that the tissue cultures were healthy and formed a monolayer that was about 90% confluent.

The media was removed from the wells, washed twice with OPTIMUM™ medium (this lacks fetal calf serum and will remove it to prevent it from disrupting liposomes) and then 0.9 ml of OPTIMUM™ medium was added to each well.

0.1 ml of the designated liposomal preparations with radioactive ciprofloxacin was added to each well on each plate (except for the controls which had 0.1 ml of sterile saline added). These were then incubated for 3, 6, or 9 hours at 37° C. At the end of each incubation period, the media was removed from the cell layers, the cells were washed 3 times with 1 ml of 0.05% Tween-20 in phosphate buffered saline, pH 7.4 to remove untaken liposomes. 0.3 ml of trypsin was added to each well, after 1 minute, 0.2 ml of this was removed and then the plates were gently banged to detach cells from the surface of the plate. 0.6 ml of 1% Triton-X 1000 (Sigma Chemical Co., St. Louis, Mich.) in PBS was added to each well to lyse the cells. The plates were rotated clockwise then anticlockwise vigorously to lyze the cells while pipetting up and down several times to disperse the cells and cause these to lyze. 0.6 ml of lysate was removed and placed in the respective labeled tube. Another 0.4 ml of Triton-X 100 in PBS was added to the wells to lyze any remaining cells and to rinse the well and this was added to the first collection.

Each sample was about 1 ml. 0.1 ml was added to AquaSol™ scintillation fluid and these were then read for radioactivity on the Easy Count™ carbon-14 program by the Wallac™ 1409 Liquid Scintillation Counter (Turks, Finland).

2.2.1 Uptake of Liposomal Formulations within Vero Tissue Cultures 2.2.1.1 Background Radiation (a) Plate with media, no cells present: 48.8 counts per minute (CPM)±2.6

(b) Plate with media, cells present: 40.4 CPM±2.7

(c) Average of (a) and (b); 43.8±2.32

2.2.1.2 Total Radiation Added to Wells

| Liposome Formulations | Radiation (CPM) |
|---|---|
| Standard liposome encapsulating C-14 ciprofloxacin | 194006 ± 79801 |
| Liposome with 2% *B. abortus* OPS encapsulating C-14 ciprofloxacin | 1763941 ± 61228 |
| Liposome with 2% *B. melitensis* LPS encapsulating C-14 ciprofloxacin | 2049765 ± 61624 |
| Liposome with 2% *B. melitensis* LPs-protein complex C-14 ciprofloxacin | 2008030 ± 13366 |
| Average of all of the above (preparations are all within 2.4% of each other on average) | 1941435 ± 46970 |

2.2.1.3 Results

| Total Radioactivity (CPM) | Radioactivity at 3 hours (CPM) | Radioactivity at 6 hours (CPM) | Radioactivity at 9 hours (CPM) |
|---|---|---|---|
| Standard liposomes 1944006 (100%) | 486773 ± 47220 (25.0%) | 89776 ± 1326 (4.6%) | 102686 ± 11167 (5.2%) |
| Liposomes with *B. abortus* OPS 1763941 (100%) | 591576 ± 113127 (33.5%) | 94575 ± 5161 (5.3%) | 74301 ± 1881 (4.2%) |
| Liposomes with *B. melitensis* LPS 2049765 (100%) | 478660 ± 51545 (23.4%) | 110990 ± 2903 (5.4%) | 79448 ± 1702 (3.9%) |
| Liposomes with *B. melitensis* LPS-protein 2008030 (100%) | 436906 ± 66099 (21.8%) | 91.256 ± 2770 (4.5%) | 79751 ± 3013 (4.0%) |

Referring to the above results, it can be seen that there is an 8.5% increase in uptake of liposomes *B. abortus* OPS compared to the standard by Vero tissue cultures. Uptake of liposomes with *B. melitensis* LPS is comparable to standard liposomes, which appears to indicate that *B. melitensis* LPS does not affect the invasiveness of the liposome in Vero tissue cultures, nor does it prevent entry of liposomes into this tissue culture.

EXAMPLE 3

Uptake of Liposome Formulations by Various Tissues in Mice 3.1 Animal Testing Balb/c mice (female, 19–21 grams, purchased from Charles River, St. Constance Quebec) had their tails warmed under a heat lamp. Then 0.1 ml of liposomal formulation was injected into the tail vein. Three formulations were tested: standard liposome-encapsulated radioactive carbon-14 (C-14) ciprofloxacin, liposomes with 2% *B. abortus* O-polysaccharide (OPS) encapsulating C-14 ciprofloxacin, and liposomes with 2% *B. melitensis* smooth lipopolysaccharide (LPS) encapsulating C-14 ciprofloxacin. Sets of 3 mice were used for each of thes 3 preparations at each of the 4 time points. At the end of the experiment, 2 mice that did not receive any radioactive liposomal formulations were also done to judge the possible presence of cross-contamination (results not included).

The mice were sacrificed at different time interval, namely 10 minutes ("time 0"), 4, 8 and 24 hours after administration of the liposome formulations. Times were staggered by 1 hour between liposomal administration to allow for the time required for the processing of tissues.

At the specified time, mice were given 0.02 ml of a 1:1 anaesthetic mixture of xylazine (Rompun™, Ayerst Laboratories, Montreal) and ketamine hydrochloride (Rogarsetic™, Rogar/STB Inc., Montreal) by intraperitoneal injection. These were anaesthetized within a minute at which time about 0.5 ml to 1.0 ml of blood was withdrawn by a heart puncture. The blood was then immediately added to a tube of 0.1 ml of 10-fold strength heparin (anti-clotting agent) solution (made by adding 1 ml of phosphate buffered saline, pH 7.2 (PBS), to a 10 ml blood collection tube). With the dose of anaesthetic and blood loss, mice perished shortly after blood collection.

Blood was left chilled at 4° C. When time permitted, the blood was transferred to an Eppendorf centrifuge tube and the level was marked on the tube. Blood samples were centrifuged (Eppendorf microfuge), and the serum was removed and placed into a separate tube. Blood cells were washed twice, each with 2 volumes of PBS, centrifugation, and then discarding the supernatant, and then PBS was added so that the original volume was maintained.

The abdomen of each sacrificed mouse was swabbed with 70% ethanol in 30% distilled water. An incision was made, and the liver was removed. This was added to a 7 ml glass tissue grinder (Wheaton, Milville, N.J.), 2 ml of PBS was added, and this was crushed manually. The content was removed and placed in a tube. Another 1 ml of PBS was added, anything remaining was either crushed or rinsed out, and the 1 ml was pooled to the previous amount.

The spleen was removed and added to a 2 ml glass tissue grinder. One ml of PBS was added, the tissue was crushed, the content was removed, another 1 ml of PBS was added to the tissue grinder, and this was added to the previous 1 ml in a tube.

The heart was processed in a manner similar to the spleen, as were the kidneys. The brain was removed from the skull and placed in 2 ml glass tissue grinder. Two ml of PBS was added, the material was crushed and then removed and placed in a tube.

A tissue grinder was assigned to each type of tissue (i.e. one for the livers) but was cleaned between use with PBS (about 10 ml) and was wiped clean. The washing process was repeated twice.

0.1 ml of each sample was added to 10 ml of scintillation fluid (Phase Combining System or PCS fluid, Amersham, Oakville, ON) into a vial. These were read on the Easy Count carbon-14 program by the Wallac 1409 Liquid Scintillation Counter (Turku, Finland).

3.2 Distribution of Radioactivity in Mice 3.2.1 Background Radiation (a) 0.1 ml of phosphate buffered saline used in this study: 108 counts per minute (CPM)

(b) Control mice (not injected with radioactive material but minor cross contamination may result due to the use of common glass tissue grinders:

| Organs | Radioactivity (CPM of 0.1 ml sample × volume/0.1 ml) |
|---|---|
| Blood cells | 0 |
| Serum | 90 |
| Spleen | 0 |
| Heart | 270 |
| Kidney | 150 |
| Brain | 300 |
| Liver | 0 |

3.2.2 Total Radiation 0.1 ml of the radioactive compounds was added to 20 ml of PBS (10 ml weights 20 grams which represents the weight of a mouse). 0.1 ml of this was added to the scintillation vial. Therefore, total radiation is count×200.

| Liposome formulations | CPM |
|---|---|
| Radioactive ciprofloxacin (original, 56.5 $\mu$Co/0.5 ml) | 24,245,400 (not used in study) |
| Standard liposomes with radioactive C-14 ciprofloxacin | 2,502,400 |
| Liposomes with *B. abortus* OPS encapsulating C-14 ciprofloxacin | 3,966,800 |
| Liposomes with *B. melitensis* LPS encapsulatiug C-14 ciprofloxacin | 2,350,000 |

3.2.3 Results

| Liposome formulations | CPM (radioactivity in 0.1 ml × volume/0.1 ml) Time 0 (10 min) | | 4 hours | | 8 hours | | 24 hours | |
|---|---|---|---|---|---|---|---|---|
| Liposomes encapsulating C-14 ciprofloxacin | B1. Cells | 4340 | B1. Cells | 1160 | B1. Cells | 0 | B1. Cells | 130 |
| | Serum | 501970 | Serum | 24310 | Serum | 6970 | Serum | 2590 |
| | Spleen | 36360 | Spleen | 22600 | Spleen | 23600 | Spleen | 1340 |
| | Heart | 30460 | Heart | 4100 | Heart | 2900 | Heart | 5680 |
| Total: 2,502,400 | Kidneys | 73940 | Kidneys | 15220 | Kidneys | 15160 | Kidneys | 8960 |
| | Brain | 2420 | Brain | 420 | Brain | 0 | Brain | 540 |
| | Liver | 19520 | Liver | 51000 | Liver | 19920 | Liver | 14560 |
| Liposomes with *B. abortus* OPS encapsulating C-14 ciprofloxacin | B1. Cells | 6060 | B1. Cells | 1240 | B1. Cells | 1120 | B1. Cells | 0 |
| | Serum | 296130 | Serum | 21640 | Serum | 52780 | Serum | 1800 |
| | Spleen | 30220 | Spleen | 14600 | Spleen | 5940 | Spleen | 1760 |
| | Heart | 33080 | Heart | 7920 | Heart | 12640 | Heart | 3300 |
| | Kidneys | 161760 | Kidneys | 8820 | Kidneys | 5100 | Kidneys | 820 |
| Total: 3,966,800 | Brain | 1960 | Brain | 840 | Brain | 240 | Brain | 180 |
| | Liver | 212720 | Liver | 31840 | Liver | 17080 | Liver | 10320 |
| Liposomes with *B. melitensis* LPS encapsulating C-14 ciprofloxacin | B1. Cells | 4620 | B1. Cells | 3400 | B1. Cells | 920 | B1. Cells | 60 |
| | Serum | 276370 | Serum | 402540 | Serum | 52750 | Serum | 1650 |
| | Spleen | 47480 | Spleen | 18500 | Spleen | 7660 | Spleen | 1220 |
| | Heart | 18740 | Heart | 32660 | Heart | 20000 | Heart | 2700 |
| | Kidneys | 113280 | Kidneys | 22400 | Kidneys | 9700 | Kidneys | 1980 |
| Total; 2,350,000 | Brain | 2660 | Brain | 580 | Brain | 980 | Brain | 240 |
| | Liver | 168300 | Liver | 201360 | Liver | 28520 | Liver | 8200 |

Referring to the above cable, it can be seen that immediately upon administration of the liposome formulations, much of the radioactivity for the standard liposome formulation remains in the serum. Liposomes made with Brucella components have a large amount of radioactivity in the serum as well, but much more radioactivity is located in the kidneys and particularly the liver, which show about a 10-fold increase. This suggests that the addition of Brucella components in liposome formulations enhances the effectiveness of the liposomes as delivery systems toward these cells. The results also suggest that liposomes composed of Brucella components target the site of infections more effectively since liver inflammations are common in brucellosis cases.

Although the invention has been described with reference to certain specific embodiments, various modifications thereof will be apparent to those skilled in the art without departing from the spirit and scope of the invention as outlined in the appended claims.

We claim:

1. A method of increasing the cellular uptake of a composition in an mammal comprising administering to said mammal said composition, wherein said composition comprises a therapeutic agent entrapped within a liposome comprising a smooth lipopolysaccharide from *Brucella melitensis*.

2. A method of claim 1, wherein said bacterial component is incorporated into or onto the membrane of said liposome.

3. A method of claim 1, wherein said liposome comprises phosphatidylcholine, cholesterol, and phosphatidylserine in a molar ratio of 7:2:1, respectively.

4. A method of claim 1, wherein said composition is taken up by non-phagocytic cells in said mammal.

5. A method of claim 1, wherein said uptake is increased in a non-phagocytic cell.

6. A method of treating a mammal against brucellosis comprising administering to said mammal a liposomal formulation comprising a smoth lipopolysaccharide from *Brucella melitensis* incorporated into or onto the membrane of said liposome to enhance the cellular uptake of said liposomal formulation by non-phagocytic cells of said mammal.

7. A method of claim 6, wherein said liposome comprises phosphatidylcholine, cholesterol, and phosphatidylserine in a molar ratio of 7:2:1, respectively.

8. A composition for controlled release and cellular uptake of an entrapped therapeutic agent comprising a liposome comprising a smooth lipopolysaccharide from *Brucella melitensis* incorporated into or onto the membrane of said liposome in an amount sufficient to provide controlled release and cellular uptake of said agent.

9. A composition of claim 1, wherein said liposome comprises phosphatidylcholine, cholesterol, and phosphatidylserine in a molar ratio of 7:2:1, respectively.

10. The method of claim 1, wherein said cellular uptake is increased in at least one of liver and kidney cells.

11. The method of claim 6, wherein said cellular uptake is increased in at least one of liver and kidney cells.

12. A composition of claim 8, wherein said cellular uptake is increased in at least one of liver and kidney cells.

* * * * *